US012685824B2

(12) United States Patent
Hammen

(10) Patent No.: US 12,685,824 B2
(45) Date of Patent: Jul. 21, 2026

(54) DETECTOR ARRANGEMENT AND POSITION DETECTOR FOR A CARTRIDGE

(71) Applicant: Sanofi, Paris (FR)

(72) Inventor: Dietmar Hammen, Frankfurt am Main (DE)

(73) Assignee: SANOFI, Paris (FR)

( * ) Notice: Subject to any disclaimer, the term of this patent is extended or adjusted under 35 U.S.C. 154(b) by 983 days.

(21) Appl. No.: 17/771,234

(22) PCT Filed: Oct. 26, 2020

(86) PCT No.: PCT/EP2020/080005
§ 371 (c)(1),
(2) Date: Apr. 22, 2022

(87) PCT Pub. No.: WO2021/083825
PCT Pub. Date: May 6, 2021

(65) Prior Publication Data
US 2022/0395645 A1      Dec. 15, 2022

(30) Foreign Application Priority Data
Oct. 28, 2019     (EP) .................................... 19306397

(51) Int. Cl.
*A61M 5/315*          (2006.01)
*A61M 5/31*           (2006.01)

(52) U.S. Cl.
CPC . *A61M 5/31568* (2013.01); *A61M 2005/3126* (2013.01); *A61M 2205/3317* (2013.01); *A61M 2205/587* (2013.01)

(58) Field of Classification Search
CPC ...... A61M 5/31568; A61M 2005/3126; A61M 2205/3317; A61M 2205/587
See application file for complete search history.

(56) References Cited

U.S. PATENT DOCUMENTS

| | | | | |
|---|---|---|---|---|
| 2010/0134303 A1* | 6/2010 | Perkins | ............... | A61M 5/1684 |
| | | | | 340/619 |
| 2013/0177455 A1* | 7/2013 | Kamen | .................. | G16H 20/17 |
| | | | | 417/313 |
| 2018/0073906 A1* | 3/2018 | Whalley | ............... | G01F 11/021 |

FOREIGN PATENT DOCUMENTS

| | | |
|---|---|---|
| JP | H02110318 A | 4/1990 |
| JP | 2005055322 A | 3/2005 |

(Continued)

OTHER PUBLICATIONS

International Preliminary Report on Patentability in International Appln. No. PCT/EP2020/080005, mailed on May 12, 2022, 9 pages.

(Continued)

*Primary Examiner* — Dung T Ulsh
(74) *Attorney, Agent, or Firm* — Bond, Schoeneck & King, PLLC

(57) ABSTRACT

The disclosure relates to a detector arrangement for detecting a position of an object with regard to a first direction, wherein the object includes a front edge and a rear edge separated from each other in the first direction and wherein the object is movable relative to the detector arrangement in the first direction. The detector arrangement includes a first detector configured to detect electromagnetic radiation, the first detector including a first detection area sensitive to the electromagnetic radiation, wherein the detection area is confined by a first detection front edge and by a first detection rear edge, wherein the first detection front edge is separated from the first detection rear edge in the first direction. At least one of the first detection front edge and the first detection rear edge extends non-parallel to at least one of the front edge and the rear edge of the object.

20 Claims, 5 Drawing Sheets

(56)        References Cited

FOREIGN PATENT DOCUMENTS

| JP | 2010505475 | A | 2/2010 |
| JP | 2015518747 | A | 7/2015 |
| JP | 2018521793 | A | 8/2018 |
| WO | WO 2011/032960 | | 3/2011 |
| WO | 2013177135 | A1 | 11/2013 |
| WO | WO 2018/046660 | | 3/2018 |

OTHER PUBLICATIONS

International Search Report and Written Opinion in International Appln. No. PCT/EP2020/080005, mailed on Nov. 13, 2020, 10 pages.
Office Action, JP Patent Application No. 2022-524971, dated Aug. 13, 2024, pp. 1-9 with pp. 1-4 being a translation.

* cited by examiner

DETECTOR ARRANGEMENT AND POSITION DETECTOR FOR A CARTRIDGE

CROSS REFERENCE TO RELATED APPLICATIONS

The present application is the national stage entry of International Patent Application No. PCT/EP2020/080005, filed on Oct. 26, 2020, and claims priority to Application No. EP 19306397.1, filed on Oct. 28, 2019, the disclosures of which are incorporated herein by reference.

TECHNICAL FIELD

The present disclosure relates to a detector arrangement and to a position detector for a cartridge filled with a medicament, wherein the detector arrangement and the position detector are operable to determine a position of a stopper being movable relative to the cartridge along a first direction. In a further aspect the disclosure relates to a cartridge equipped with a position detector. In further aspects the disclosure relates to a drug delivery device configured to accommodate a cartridge filled with the medicament and being further equipped with a position detector.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors meet a number of user-specific requirements. For instance, with patient's suffering chronic diseases, such like diabetes, the patient may be physically infirm and may also have impaired vision. Suitable drug delivery devices, especially intended for home medication, might need to be robust in construction and easy to use. Manipulation and general handling of the device and its components can be designed to be intelligible and easy understandable. Such injection devices should provide setting and subsequent dispensing of a dose of a medicament of variable size. A dose setting as well as a dose dispensing procedure can be designed to be easy to operate and to be unambiguous.

SUMMARY

Devices include a housing or a particular cartridge holder, adapted to receive a medicament container, e.g. in form of a cartridge at least partially filled with the medicament to be expelled. The device further includes a drive mechanism, usually having a displaceable plunger or piston rod to operably engage with a bung or piston of the medicament container or cartridge. By means of the drive mechanism and its piston rod, the bung or piston of the cartridge is displaceable in a distal or dispensing direction and may therefore expel a predefined amount of the medicament via a piercing assembly, e.g., in form of an injection needle, connected to or is releasably connectable with an outlet end of the medicament container. With reusable drug delivery devices an empty cartridge is replaceable by a filled one. In contrast to that, drug delivery devices of disposable type are to be entirely discarded when the medicament in the cartridge has been dispensed or used-up.

The amount of medicament remaining in a cartridge while the cartridge is arranged inside a drug delivery device can be determined. There have been described methods for determining the position of the stopper in a medicament ampoule in a medical appliance by means of a light source and photosensitive sensor surfaces.

When making use of a number of discrete photosensitive sensors, such as a photodiodes, arranged along in a row extending along a moving direction of a stopper of a cartridge there is an inevitable gap between consecutive or adjacently arranged photodiodes. When an edge of a stopper coincides or overlaps with such a gap, the precision of the position determination may suffer. On the one hand, use of rather simple and cost efficient light detectors, such as an array of light detectors, e.g., in form of photodiodes, is beneficial for use with disposable injection devices. However, the spatial resolution of the position detection is limited by the gap size between adjacently arranged photodiodes.

An improved detector arrangement and an improved position detector can be provided to allow to increase the precision of the position detection and to increase the spatial resolution of the detector arrangement or position detector by simultaneously avoiding a substantial increase of costs for manufacturing and assembly. Moreover, the solution can be implementable with rather low or moderate costs on the basis of low-cost discrete light-sensitive elements or detectors.

In one aspect there is provided a detector arrangement for detecting a position of an object with regard to a first direction of movement. The object includes a front edge and a rear edge. The front edge is separated from the rear edge in or along the first direction. The object is movable relative to the detector arrangement with regard to the first direction. The object is movable relative to the detector arrangement along the first direction. The object might be movable relative to the detector arrangement only along or only with regards to the first direction.

The detector arrangement includes a first detector. The first detector is configured or operable to detect electromagnetic radiation. The first detector includes a first detection area. The first detection area is sensitive to the electromagnetic radiation. The first detection area is confined by a first detection front edge and by a first detection rear edge. The first detection front edge is separated from the first detection rear edge in the first direction or with regard to the first direction. Typically, with regard to the first direction of movement of the object relative to the detector arrangement the first detection front edge and the first direction rear edge form or constitute a distal and a proximal edge or border of the first detection area, respectively.

At least one of the first detection front edge and the first detection rear edge extends non-parallel to at least one of the front edge and the rear edge of the object. Typically, at least one of the first detection front edge is oriented or extends at a non-zero angle with regard to the extension or elongation of at least one of the front edge and the rear edge of the object. Typically, at least one of the first detection front edge and the first detection rear edge is tilted or slanted with regards to the orientation or extension of at least one of the front edge and the rear edge of the object.

With some examples, both, the first detection front edge and the first detection rear edge extend non-parallel or at a non-zero angle with regards to at least one of the front edge and the rear edge of the object. With some examples the first detection front edge and the first detection rear edge extend both non-parallel or at a non-zero angle with regard to both, the front edge and the rear edge of the object.

With some examples, the first detection front edge and the first detection rear edge extend parallel to each other. Additionally or alternatively, also the front edge and the rear edge of the object extend parallel to each other.

The non-parallel or tilted arrangement or orientation of at least one of the first detection front edge of the first detection rear edge with regards to at least one of the front edge and the rear edge of the object provides the benefit that a mutual coverage or spatial overlap of the object and the first detector is subject to a gradual, constant and smooth variation as the object is moved along the first direction relative to the first detector. Situations and configurations in which one of the rear edge and the front edge abruptly reaches or arrives in a non-overlapping configuration with regard to one of the first detection rear edge and the first detection front edge can be effectively avoided. In this way, a spatial resolution of the detector arrangement can be improved without the necessity to reduce a gap size between adjacently arranged detectors and/or without the necessity to reduce the size of discrete detectors of the detector arrangement.

In numerous examples the first detection front edge of the first detector substantially faces in the first direction of movement of the object. The first detection rear edge substantially faces in the opposite direction. The front edge of the object may coincide with a front face of the object. The rear edge of the object may coincide with a rear face of the object. The front face of the object typically includes a surface normal that extends substantially parallel to the first direction. The surface normal of the rear face of the object includes a surface normal that extends substantially parallel to a direction diametrically opposite to the first direction.

A perpendicular bisector of the first detection front edge extends at a non-zero angle with regard to the first direction. The same is valid for a respective perpendicular bisector of the first detection rear edge. The angle between the perpendicular bisector of the first detection front edge and the first direction may be in a range of 1° to 45°. It may be in a range between 1° and 30°. It may be in a range between 1° and 20°. It may be in a range between 1° at 10°. It may be in a range between 2° and 5°. It may be in a range between 5° and 15°. It may be in a range between 5° and 10°.

The particular angle between the perpendicular bisector of the first detection front edge or the first detection rear edge with the first direction and hence with a surface normal of at least one of the front face and the rear face of the object depends on the overall geometry of the first detection area of the first detector. It may further depend on a gap size between the first detector and an adjacently arranged second detector. The non-zero angle may further depend on the size or expansion of the first detection area of the first detector along or with regards to a second direction extending substantially perpendicular to the first direction.

According to a further example the detector arrangement includes a second detector. The second detector is configured to detect the electromagnetic radiation. The second detector is separated from the first detector in the first direction. A gap is formed between the first detector and the second detector. Hence, the first detector is separated from the second detector by a gap. Both, the first detector and the second detector are individually connected to a processor or a signal processing device in a signal transmitting way. The first detector and the second detector are each configured to detect electromagnetic radiation and to generate and transmit at least one electrical signal being indicative of at least one of the intensity and the wavelength of the electromagnetic radiation present at the respective detection area of the first or second detector.

The second detector can include a second detection area. The first detector and the second detector may be of substantially equal shape and configuration. The second detector may be identically shaped and/or identically configured to the first detector. The second detector is typically arranged adjacent to the first detector with the gap in between.

As the object is moved relative to the detector arrangement in the first direction electromagnetic radiation may be reflected or absorbed by the object. Due to the movement of the object relative to the detector and the interaction between the object and electromagnetic radiation an intensity and/or a spatial distribution of electromechanical radiation on the first detector and/or on the second detector is subject to a measurable change as the object is moved along the first direction.

The object may be implemented as a stopper slidably arranged inside a tubular shaped barrel of a medicament container. The barrel may include a material substantially transparent for the electromagnetic radiation. The object or stopper may absorb the electromagnetic radiation. Insofar and as the object is moved relative to the detector arrangement, a shadow of the stopper may be present on the first detector and/or on the second detector. The detector arrangement includes numerous detectors or even an elongated row or an array of detectors extending along the first direction. As the object is subject to a movement in the first direction, a spatial overlap of the object and/or of its shadow on the numerous detectors of the detector arrangement is subject to a measurable change.

The detector arrangement can be operated in an absorption mode, wherein electromagnetic radiation absorbed by the object is detected. With other implementations the detector arrangement is particularly configured to detect a position of electromagnetic radiation on the numerous detectors that is reflected by the moving object. As the object moves, electromagnetic radiation reflected by the object moves accordingly relative to the numerous detectors of the detector arrangement.

In a further example, the second detector is arranged in line to the first detector or with regards to the first direction. The first detector and its first detection area include a first side edge and an oppositely located second side edge. The first and the second side edges may be separated in a second direction that extends parallel to the first direction. The oppositely arranged first and second side edges may confine the detection area with regards to the second direction. The second direction and the first direction lie in the plane or extend parallel to the surface of the first detection area. The second detector has corresponding first and second side edges. When the second detector is arranged in line to the first detector, an imaginary extension of the first side edge of the first detector aligns and/or overlaps with the first side edge of the second detector. Also, an imaginary elongated extension of the second side edge of the first detector may coincide with a second side edge of the second detector.

When the detector arrangement includes numerous detectors, e.g. at least 5, 10 or even more than 100 discrete detectors, all detectors may be arranged in line along or with regard to the first direction. The detector arrangement may include an elongated row of discrete and mutually separated detectors.

With another example the second detector includes a second detection area that is sensitive to the electromagnetic radiation. The second detection area is confined by a second detection front edge and by a second detection rear edge. The second detection front edge is separated from the second detection rear edge in the first direction. At least one of the second detection front edge and the second detection rear edge extends non-parallel to at least one of the front edge and the rear edge of the object.

As such, the second detector may be of substantially equal shape and orientation compared to the first detector. The second detector is arranged at a well-defined offset from the first detector along or in the first direction. Insofar, the second detection rear edge faces towards the first detection front page. When the detector arrangement includes a row of numerous individual detectors, all detectors may include an equal or similar shape and may be arranged in line or flush with regard to the first direction. They may be equidistantly arranged in the first direction. In this way, electrical signals obtained from individual detectors of a detector row or detector array are directly comparable and can be processed in an identical manner by a processor or signal processing device.

According to a further example the first detection front edge at least in sections extends parallel to the first detection rear edge. The first detection front edge is of rather straight shape. The same is valid for the first detection rear edge. With typical implementations, the entirety of the first detection rear edge extends parallel to the entirety of the first detection front edge. The same may apply to all further detectors of the detector arrangement.

Moreover and with other examples, the first detection front edge entirely or at least in sections extends parallel to the second detection rear edge. The first detection rear edge may also extend entirely or at least in sections parallel to the second detection front edge.

With some examples, each detector of the detector arrangement may include a rhomb-like structure wherein opposite located edges of the detection area extend substantially parallel. Mutually adjoining edges extend at an angle not equal to 90°. The detection area includes four corners or edges, wherein the diagonals of opposite corners differ in length.

With the above-described repetitive and equidistant arrangement of identically shaped detectors along the first direction it can be achieved, that for any conceivable position of at least one of the front edge and the rear edge of the object there will be an unequivocal signal from the numerous detectors. During a movement of the object in the first direction and as soon as the object leaves an area of coverage or a spatial overlap with the first detector it is immediately in the area of coverage or in a spatial overlap with an adjacently arranged detector. With the rhomb-like implementation of the detectors of the detector arrangement the detector arrangement is substantially void of any blind spots or areas. Insofar, the spatial resolution of the detector arrangement can be increased without a decrease of the gap size and/or without a decrease of the spatial size of the numerous detectors.

The first detection area of the first detector is operable and configured to integrate the amount of electromagnetic radiation present across the first detection area. With a given constant intensity of the electromagnetic radiation, the electric signal generated by the first detector is subject to a constant change as the detection area becomes continually shaded. A degree of shading or a degree of covering of the first detection area directly reflects in the magnitude of the signal produced by the first detector.

According to another example the second detection rear edge includes a first end adjoining a first lateral side edge of the second detection area. The second detection rear edge includes a second end adjoining a second lateral side edge of the second detection area. A position of the first end of the first detection front edge with regard to the first direction overlaps or adjoins a position of the second end of the second detection rear edge with regards to the first direction. Alternative to this, a position of the second end of the first detection front edge with regard to the first direction overlaps or adjoins with a position of the first end of the second detection rear edge with regards to the first direction.

This criterion provides a definition of the gap size between first and second detectors in the first direction. The first side edge of the first detection rear edge overlaps or adjoins the second side edge of the second front edge of the second detector as seen in the first direction. In other words the first end of the second detection rear edge adjoins or overlaps with the second end of the first detection front edge as seen in the first direction. Alternatively, the second end of the second detection rear edge adjoins or overlaps with the first end of the first detection front edge as seen in the first direction.

With the front edge and the rear edge of the object extending substantially perpendicular to the first direction and hence to the direction of movement of the object relative to the detector arrangement it can be ensured, that the rear edge or front edge of the object is always in the coverage or in spatial overlap with one of the first detection area and the second detection area.

According to a further example at least one of the first detection front edge of the first detection rear edge extends at an angle b with regard to the first direction. A size G of the gap substantially equals $G=L \sin(90°-b)$, with L being a length of one of the first detection front edge and the first detection rear edge. With the above formula, a well-defined relationship between the angle b, the gap size G and the length L of the detection front edge or detection rear edge is given.

With a further example, the detector arrangement includes numerous first detectors forming a longitudinal detector row extending along the first direction. Typically, each one of the detectors includes a detection front edge, which in view of the first direction is a leading edge, and a section rear edge, which in view of the first direction is a trailing edge.

In another aspect the disclosure relates to a position detector for determining a position of a stopper in a cartridge with regards to a first direction. The stopper is slidably arranged inside the cartridge with regard to the first direction. The stopper can be moved in the first direction relative to a barrel of the cartridge. The cartridge is configured to accommodate or to be filled with a liquid medicament. The position detector includes a flexible substrate. The flexible substrate is configured to become wrapped around the barrel of the cartridge. The position detector further includes a detector arrangement as described above and being arranged on the flexible substrate.

The position of the object as defined above is the position of the stopper in relation to the detector arrangement. Here, the stopper of the cartridge represents the object of the above defined detector arrangement. The position detector further includes at least one light source configured to emit electromagnetic radiation onto or through the barrel of the cartridge. The position detector further includes a microprocessor arranged on the flexible substrate. The microprocessor is connected to the detector arrangement. The microprocessor is operable to determine a position of the stopper with regard to the first direction on the basis of at least one electric signal received from the detector arrangement when exposed to the electromagnetic radiation. The detector arrangement is configured and/or operable to generate and to transmit numerous electric signals, wherein each one of the electric signals is indicative of the electromagnetic radiation present on a respective detector of numerous detectors of the detector arrangement.

The at least one light source may be ambient light. Alternatively, the at least one light source may include at least one light-emitting element that may be arranged offset from the flexible substrate.

The position detector may be configured to operate in a transmission mode, wherein a shadow of the cartridge on the detector arrangement is detected and wherein the shadow of the stopper is detectable by the detector arrangement. With other examples, the position detector is configured to operate in a reflection mode, wherein electromagnetic radiation reflected by the stopper is detected and wherein the detected electromagnetic signals are indicative of the position of the stopper relative to the barrel.

With either implementation the barrel is transparent for the electromagnetic radiation for which the detectors of the detector arrangement are sensitive. Also, the medicament located inside the barrel may be transparent for the electromagnetic radiation.

According to a further example the at least one light source is arranged on the flexible substrate. The at least one light source includes numerous light-emitting elements that are separated from each other in the first direction. There may be provided numerous light-emitting elements, such as light-emitting diodes (LED).

The light source may include a light empty diode (LED) or a row of numerous LED providing a well-defined spatial distribution of electromagnetic radiation, e.g. of visual, UV or infrared light. The wavelength or spectrum of the electromagnetic radiation emitted by the at least one light source and detected by the at least one detector of the detector arrangement may be adapted in accordance to the transmission or absorption properties of the barrel, the stopper and the medicament located inside the cartridge.

The first detector or all of the numerous detectors of the detector arrangement may include commercially available photodetectors, such as photoresistors or photodiodes. Such detectors for electromagnetic radiation are available at rather low or moderate costs. Insofar, a rather low-cost detector arrangement can be provided that is even implementable as a disposable detector arrangement. Hence, the position detector may be inseparably connected to the cartridge and may be intended to become discarded once the content of the cartridge has been expelled, withdrawn or used up.

With another example the at least one light source includes at least one light-emitting element and a longitudinally extending light guiding structure. The light guiding structure is optically coupled with the at least one light-emitting element. The longitudinally extending like guiding structure extends substantially parallel to the first direction. In this way, a rather homogeneous and well-defined illumination of the cartridge can be provided even with a limited number of light-emitting elements. The light guiding structure may include a fluorescent or phosphorescent stripe that is excited by the at least one light-emitting element. Moreover, it is conceivable, that at least two or even more light-emitting elements are optically coupled to the light guiding structure.

In another aspect the disclosure relates to a cartridge for a liquid medicament. The cartridge includes an elongated barrel extending along a first direction. The cartridge further includes a stopper arranged inside the barrel and being displaceable relative to the barrel along the first direction for expelling or for withdrawing the liquid medicament. The stopper may represent or may provide a proximal seal of the cartridge. The cartridge further includes a position detector as described above that is wrappable around the cartridge. With some examples, the position detector is actually wrapped around the barrel of the cartridge. The position detector may be inseparably, e.g. adhesively fixed to the outside of the barrel of the cartridge.

In this way, a cartridge with an improved detector arrangement can be provided offering a precise measurement of the stopper position along the first direction, wherein the stopper position relative to the barrel is directly indicative of the amount of medicament inside the cartridge.

With a further example the at least one light source is located diametrically opposite to the detector arrangement when the position detector is wrapped around the barrel. The stopper is located between the at least one light source and the detector arrangement of the position detector when the position detector is wrapped around the barrel. The light source and the detector arrangement extend substantially parallel to each other on the flexible substrate. Both, the detector arrangement and the light source may extend along the first direction. The first direction may coincide with a longitudinal direction of the tubular-shaped barrel. It may also coincide with a central axis of symmetry of the tubular-shaped barrel.

The at least one light source and the detector arrangement are separated by a predefined distance from each other along the second direction. In the unwrapped, hence in a substantially planar-shaped initial configuration of the flexible substrate, the first direction and the second direction coincide with the plane of the substrate. The distance between the at least one light source and the detector arrangement with regards to the second direction is typically governed by the diameter of the barrel. The larger the diameter, the larger will be the distance between the at least one light source and the detector arrangement of the position detector.

In another aspect the disclosure relates to a drug delivery device comprising a drive mechanism. The drive mechanism includes a piston rod configured to expel a liquid medicament from a cartridge. The cartridge includes a barrel and a stopper. The stopper is arranged inside the barrel and the stopper is displaceable relative to the barrel along a first direction for expelling the liquid medicament. The drug delivery device includes a housing configured to accommodate the cartridge. The drug delivery device further includes a position detector as described above.

With a further example the drug delivery device includes a cartridge for a liquid medicament as described above, wherein the position detector is wrapped around the barrel of the cartridge and/or wherein the position detector is inseparably connected to the cartridge, e.g. by an adhesive.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound includes at least one peptide for the treatment and/or prophylaxis of diabetes mellitus or complications associated with diabetes mellitus such as diabetic retinopathy, wherein in a further embodiment the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-   Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\varepsilon$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\varepsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the scope of the disclosure. Further, it is to be noted, that any reference numerals used in the appended claims are not to be construed as limiting the scope of the disclosure.

BRIEF DESCRIPTION OF THE FIGURES

In the following, numerous examples of the container and of an injection device will be described in greater detail by making reference to the drawings, in which.

DETAILED DESCRIPTION

Figure 1:
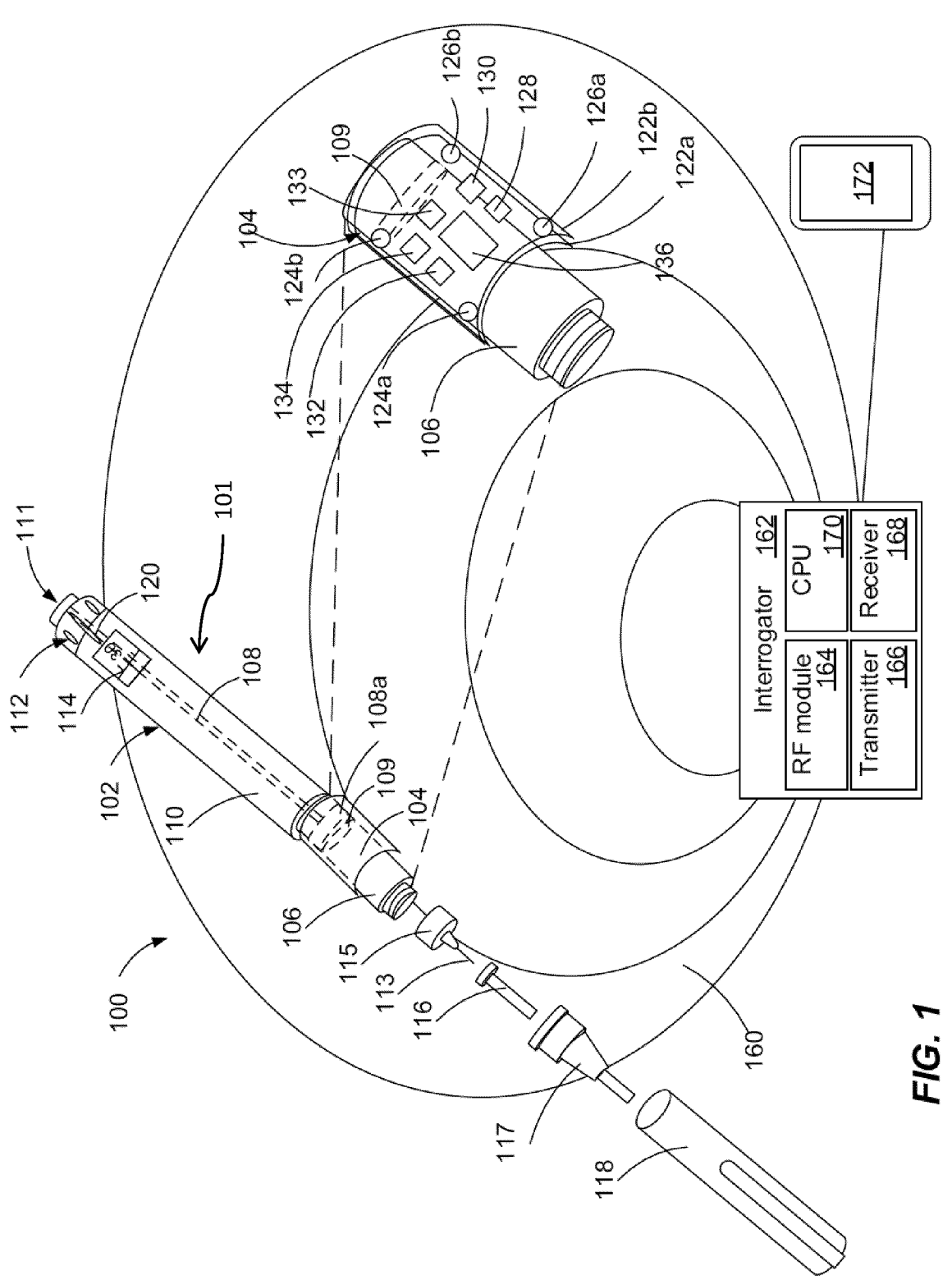
FIG. 1 shows an example of an injection device.

FIG. 1 illustrates an exploded view of an example drug delivery device 100 including an injection device 102 with a position detector 104. The position detector 104 can be implemented as a flexible smart label that can be used to share data across a healthcare continuum. In FIG. 1 the position detector 104 is attached to a cartridge 106. The injection device 102 can be a pre-filled, disposable injection pen or the injection device 102 can be a reusable injection pen. The injection device 102 can include the housing 110 and contains the cartridge 106, to which a needle assembly 115 that includes a needle 113 can be affixed. The injection device 102 includes a drive mechanism 101 having a piston rod 108 configured to expel or to withdraw a dose of the medicament from the cartridge 106. A portion of the housing and/or of the cartridge 106 can be made of a material transparent for light beams in at least one of the visible spectrum, the UV spectrum and the infrared spectrum.

The needle 113 is protected by an inner needle cap 116 and an outer needle cap 117, which in turn can be covered by a cap 118. The cartridge 106 can be configured to contain a liquid medicament. A dose of the contained medicament can be ejected from the injection device 102 by turning the dosage knob 112, and the selected dose is then displayed via dosage window 114, for instance in multiples of so-called International Units (IU), wherein one IU is the biological equivalent of about 45.5 micrograms of pure crystalline insulin (1/22 mg). An example of a selected dose displayed in dosage window 114 may for instance be 30 IUs, as shown in FIG. 1. In some implementations, the selected dose can be displayed differently, for instance by an electronic display (e.g., the dosage window 114 may take the form of an electronic display).

Turning the dosage knob 112 can cause a mechanical click sound to provide acoustical feedback to a user. The numbers displayed in dosage window 114 can be printed on a sleeve that is contained in housing 110 and mechanically interacts with a plunger head 108a that is fixed at the end of the piston rod 108 and pushes the stopper 109 of the cartridge 106. The plunger head 108a is configured to expel a portion of the fluid by displacing the stopper 109 contained within the cartridge 106, such that a position of the stopper 109 is associated with an amount of the fluid within the injection device 102. When the needle 113 is stuck into a skin portion of a patient, and when then the injection button 111 is pushed, the insulin dose displayed in display window 114 can be ejected from injection device 102. When the needle 113 of injection device 102 remains for a certain time in the skin portion after the injection button 111 is pushed, a high percentage of the dose is actually injected into the patient's body. Ejection of the insulin dose can generate a mechanical click sound, which can be different from the sounds produced when using dosage knob 112.

As described in further detail below, the position detector 104, e.g. in form of a smart label, can include a flexible substrate 105. The flexible substrate 105 may include an adhesive layer 122a and a carrier layer 122b. The carrier layer 122b can include electronic components such as LEDs and photodiodes that can be used to sense characteristics of the injection device 102 such as the stopper position and/or amount of medicament in the cartridge 106.

The injection device 102 may be used for several injection processes until either the cartridge 106 is empty or the expiration date of injection device 102 (e.g. 28 days after the first use) is reached. Before using injection device 102 for the first time, it may be necessary to perform a so-called "prime shot" to remove air from cartridge 106 and needle 113, for instance by selecting two units of insulin and pressing injection button 111 while holding injection device 102 with the needle 113 upwards.

The position detector 104 and hence the flexible smart label can be configured to attach to a variety of surface geometries, including planar and non-planar geometries (e.g., curved, angled or a combination thereof) to continuously or periodically monitor the amount of fluid that is contained within the injection device 102 and delivered by the injection device 102. The position detector 104 can be associated with an identifier. The identifier can be a random number r that can be encoded in a machine-readable medium, such as radio frequency identification (RFID) data, in a 2-dimensional (2D) bar code, and/or in a QR code included with the item. The random number r can be associated with the position detector 104, e.g. the flexible smart label and can be used to uniquely identify the position detector 104 and corresponding flexible smart label-level data stored in a repository.

The position detector 104 or the smart label can be configured to possess enhanced mechanical, thermal, electrical, optical, and physical properties such as flexibility, surface hardness, thermal conductivity, dielectric constant, abrasion resistance, optical transmissivity, permeability, chemical stability, bond strength, and other properties. For example, the position detector 104 and hence the flexible smart label can have a Young's Modulus of from about 0.5 to about 5 GPa, a dielectric constant of from about 2 to about 5, and a Rockwell hardness of from about 35 to about 120. The flexible substrate 105 can include an adhesive layer 122a and a carrier layer 122b. The adhesive layer 122a can be configured to removably attach the flexible smart label to a surface of the injection device 102. The adhesive layer 122a can be urethane resin-based, silicone resin-based, vinyl resin-based, polyester resin-based, synthetic rubber-based, and natural rubber-based adhesives, etc. In some implementations, the adhesive layer 122a can include a non-attachable corner to enable the removal of the position detector 104 from the injection device 102.

A plurality of flexible components can be attached to the carrier layer 122b. The flexible components can include printed electronics generated using functional inks for printing the electronics defining the position detector 104. The plurality of flexible components includes light-emitting elements 124a and 124b such as light-emitting diodes (LEDs), detectors 201, 202, 203, e.g. implemented as photodiodes, a microprocessor 128, an antenna 130, a temperature sensor 132, a power management unit 134, and a display. The light-emitting elements 124a and 124b can have a variety of geometries, such as circles, rectangles and/or stripes (having one side significantly larger than the other side). In some implementations, a single light-emitting element 124a and hence a single LED can be used. The single LED can be a stripe. In other implementations, multiple light-emitting elements 124a and 124b can be arranged as an array of LEDs, including at least two LEDs. The array of light-emitting elements 124a and 124b, hence the array of LEDs can be a linear array or a rectangular array.

The light-emitting element 124a and 124b can be attached to the flexible substrate 105 in a first position that can define a longitudinal arrangement of the light-emitting elements. The light-emitting elements 124a and 124b can be configured to emit a light signal in a direction based on the first position towards the detectors 201, 202, 203 through an optically transparent wall of the barrel 107 of the cartridge 106 or of the housing 110. In some implementations, the light-emitting elements 124a and 124b can emit an invisible light signal (e.g., in the infrared spectrum).

The numerous detectors 201, 202, 203, e.g. implemented as photodiodes 126a, 126b can have a variety of geometries, such as a rhombus or a rhomb-like rectangle. The detectors 201, 202, 203 can have a pixel size of tens of μm. A stripe photodiode can have a length in the order of millimeters that is shorter than the length of the piston rod 108 or the cartridge 106. In some implementations, a single photodiode can be used. The single photodiode 126a, 126b can be a stripe (e.g., autoinjector). In other implementations, detectors 201, 202, 203, e.g. in form of multiple photodiodes 126a and 126b can be arranged in a row or as an array of photodiodes, including at least two photodiodes (e.g., four, six or hundreds of photodiodes). The photodiodes 126a and 126b can be arranged in a regular pattern with equal distances between the photodiodes. The photodiodes 126a and 126b can be arranged in an irregular pattern that can have two distances between the photodiodes, one of the distances being half of the other distance to increase the detection accuracy.

Figure 7:
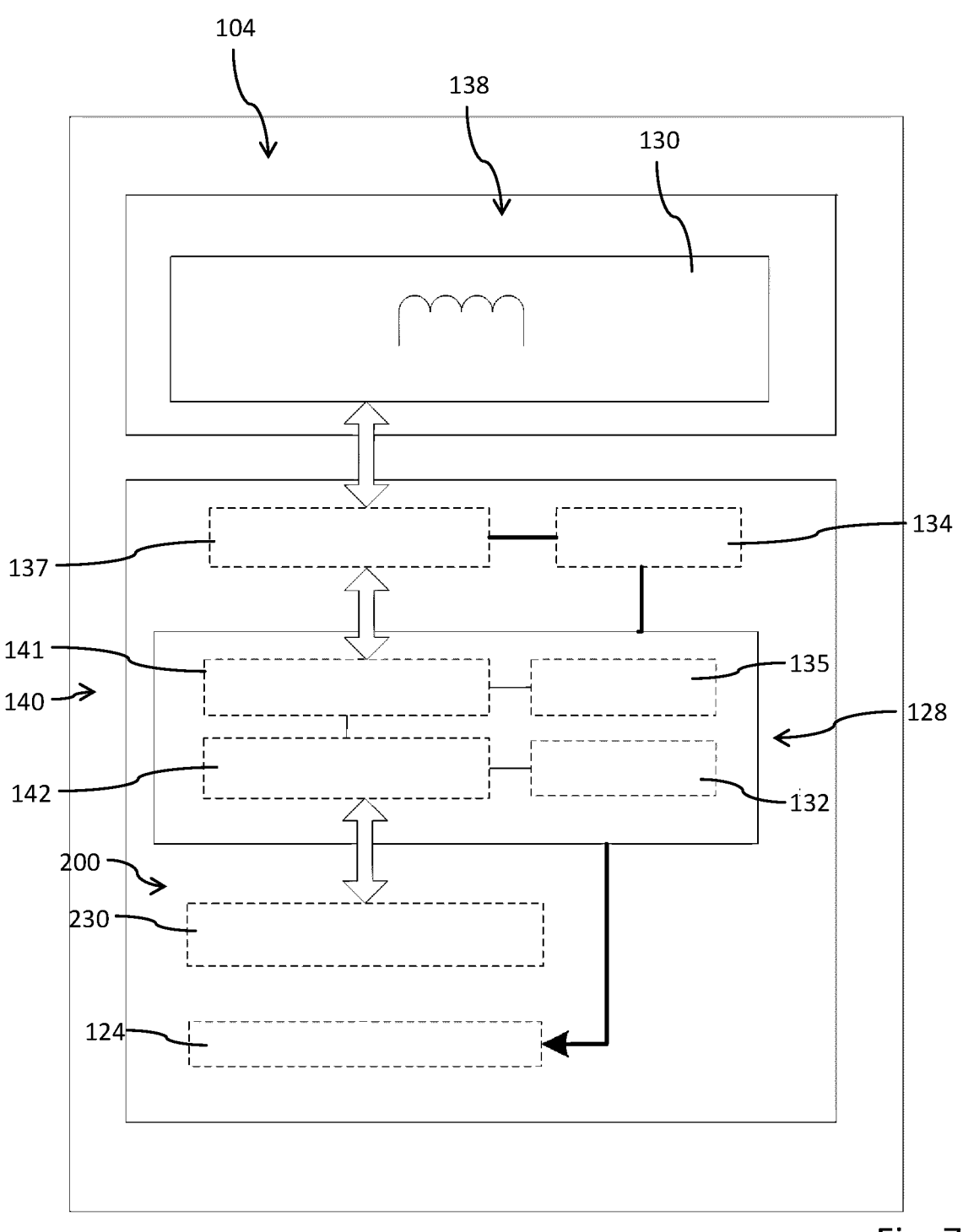
FIG. 7 shows a block diagram of one example of the position detector.

FIGS. 1 and 7 illustrate block diagrams of an example the position detector 104 and/or of the respective smart label. The flexible smart label can be an electronic printed label. The flexible smart label can provide remote identification and telemetering. The flexible smart label can include an energy harvesting and data transfer module 138 and a functional electronic module 140.

The energy harvesting and data transfer module 138 includes an antenna 130, which is mounted within the flexible smart label to receive an exciter signal when being in an NFC field 160. The antenna 130 can receive energy (e.g., radio frequency (RF) energy) from the NFC field 160 (e.g., interrogation field) created by the transmitter 166 in the interrogator 162 of the NFC field 160. In some implementations, through the mechanism of modulated RF backscatter, in which the impedance connected to the antenna 130 may be periodically modulated by an electronic code generator circuit 133 within the position detector 104 or the smart label, the position detector 104 or the smart label returns part of that energy in the form of a coded reply signal to the receiver 168 in the interrogator 162. The antenna 130 generates a signal to multiple components within functional electronic module 140, such as a clock, a frequency tuning module, and a rectifier/regulator. A signal from the antenna 130 is transmitted through communication front end 137 to a frequency tuning module to tune the frequency of the antenna 130. Typically, a signal from the antenna 130 is transmitted to the clock to generate a clock signal as input for a divider and synchronization module. The divider and synchronization module controls the sequencing of the cyclical transmitted data stream for modulation encoding, which can modulate the amplitude and/or frequency of the signal before communicating the signal to the rectifier.

The communication front end 137 and the processor 128 may be further connected to a power management unit 134. The power management unit 134 may include an onboard battery. The power management unit 134 may include a power source. The power source includes at least one of an integrated flexible battery or super capacitor. The power management unit 134 may include an own power source 134 can be configured to supply energy to the flexible components of the flexible smart label under particular conditions, such as when the fluid delivery system 100 is within an NFC field 160. The NFC field 160 can be generated by an interrogator 162. The interrogator 162 can include a RF module 164, a transmitter 166, a receiver 168, and a processor 170. The interrogator 162 can be configured to communicate with an external device 172 that is configured to display the data received from the flexible smart label.

The functional electronic module 140 includes a central processing unit 141, a memory 135, an optional temperature sensor 132 and an analog-digital converter 142. The analog-digital converter 142 is connected to the detector row 230, the detail of which described in greater detail below.

Data generated by the functional electronic module 140 can be an N-bit data including data associated with the electric signal generated by the detectors 201, 202, 203 of the detector row 230 indicating the amount of fluid within the cartridge 106 or within injection device 102.

For example, the data associated with the electric signal generated by the detector arrangement 200 detector can be formatted using digital shift-registers and counters to reduce the amount of data transmitted to a minimum, according to ISO 14443 Type A RFID standard. For example, the electric signal generated by the detectors 201, 202, 203 can be formatted as a row pattern that is stored in a several N-bit shift register.

Figures 2, 3:
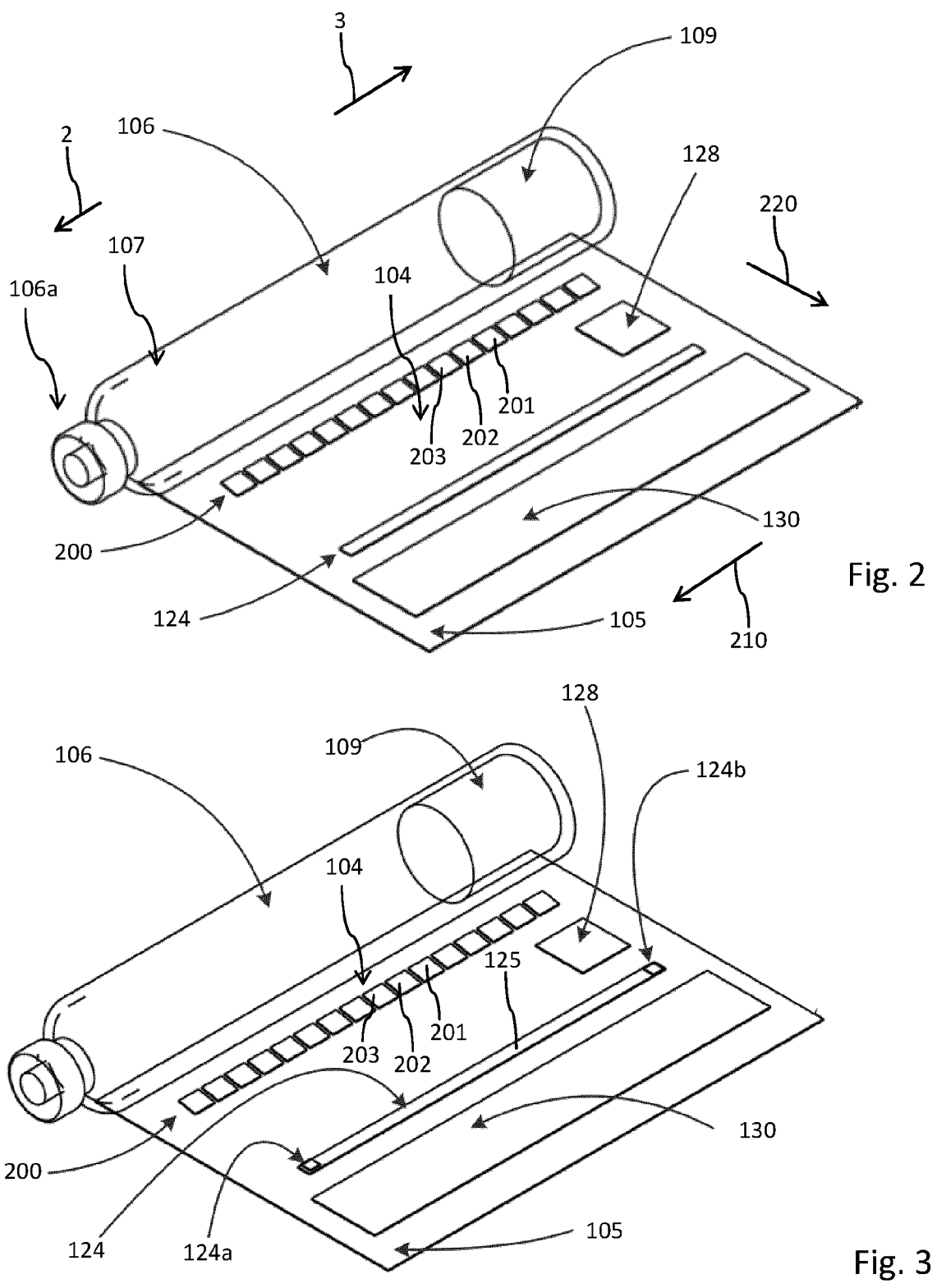
FIG. 2 shows a first example of a position detector.
FIG. 3 shows another example of a position detector.

In FIG. 2 one example of a cartridge 106 equipped with a position detector 104 is illustrated. The position detector 104 includes a flexible substrate 105, e.g. a polymeric base layer. The flexible substrate 105 may include a flexible plastic foil configured to become wrapped around the barrel 107 of the cartridge 106. The barrel 107 is of tubular shape. It includes a hollow interior that is sealed in a proximal direction by a stopper 109. The stopper 109 may include a rubber stopper and may seal the interior of the barrel 107 in proximal direction. In distal direction 2, hence at a distal end the cartridge 106 includes an outlet 106a that is connectable to the needle 113 or to a medicament guiding structure in a fluid transferring way.

As illustrated in FIGS. 2 and 3 the position detector 104 includes an elongated array or row 230 of numerous discrete detectors 201, 202, 203. The detectors 201, 202, 203 of the position detector 104 are equidistantly arranged along the first direction 210. At a predefined distance with regards to a second direction 220 there is provided an elongated light source 124 on the flexible substrate 105. The light source 124, as illustrated in FIG. 2, includes an elongated strip of light-emitting diodes. The light source 124 may include an elongated strip of organic light-emitting diode (OLED). The elongated light source 124 and the detector row 230 may extend substantially parallel along or in the first direction 210.

In the further example as illustrated in FIG. 3 the light source 124 includes at least one or numerous light-emitting elements 124a, 124b that are optically coupled to a light guiding structure 125. Here, the light guiding structure 125 includes an elongated strip of a light-emitting material. The light guiding structure 125 may include an elongated strip of a luminous material. The light guiding structure 125 may include a phosphorescent or fluorescent material. At least one longitudinal end of the light guiding structure 125 is optically coupled with at least one of the light-emitting elements 124a, 124b. The light-emitting elements 124a, 124b may include conventional LEDs or OLEDs.

The position detector 104 is optionally equipped with an antenna 130 as described above. The position detector 104 further includes a processor 128 that is connected to the detector arrangement 200 and/or to the numerous detectors 201, 202, 203, individually. One configuration of the detector arrangement 200 is illustrated in more detail in FIGS. 4-6. As shown there the detector arrangement 200 includes numerous detectors 201, 202, 203. The detectors 201, 202, 203 each include a detection area 208. In the presently illustrated example the detection area 208 is of rhomb-like shape.

The detection area 208 of the first detector 201 is confined in the first direction 201 by a first detection front edge 211 and by a first detection rear edge 212. The first detection front edge 211 may represent the distal edge of the detection area 208. The first detection rear edge 212 may represent the proximal edge of the detection area 208. The detection area 208 is further confined by two oppositely located side edges, namely a first side edge 214 and a second side edge 215. The first side edge 214 adjoins a longitudinal first end 211a of the first detection front edge 211. The oppositely located second side edge 215 adjoins a second longitudinal end 211b of the first detection front edge 211.

Figures 4, 5, 6:
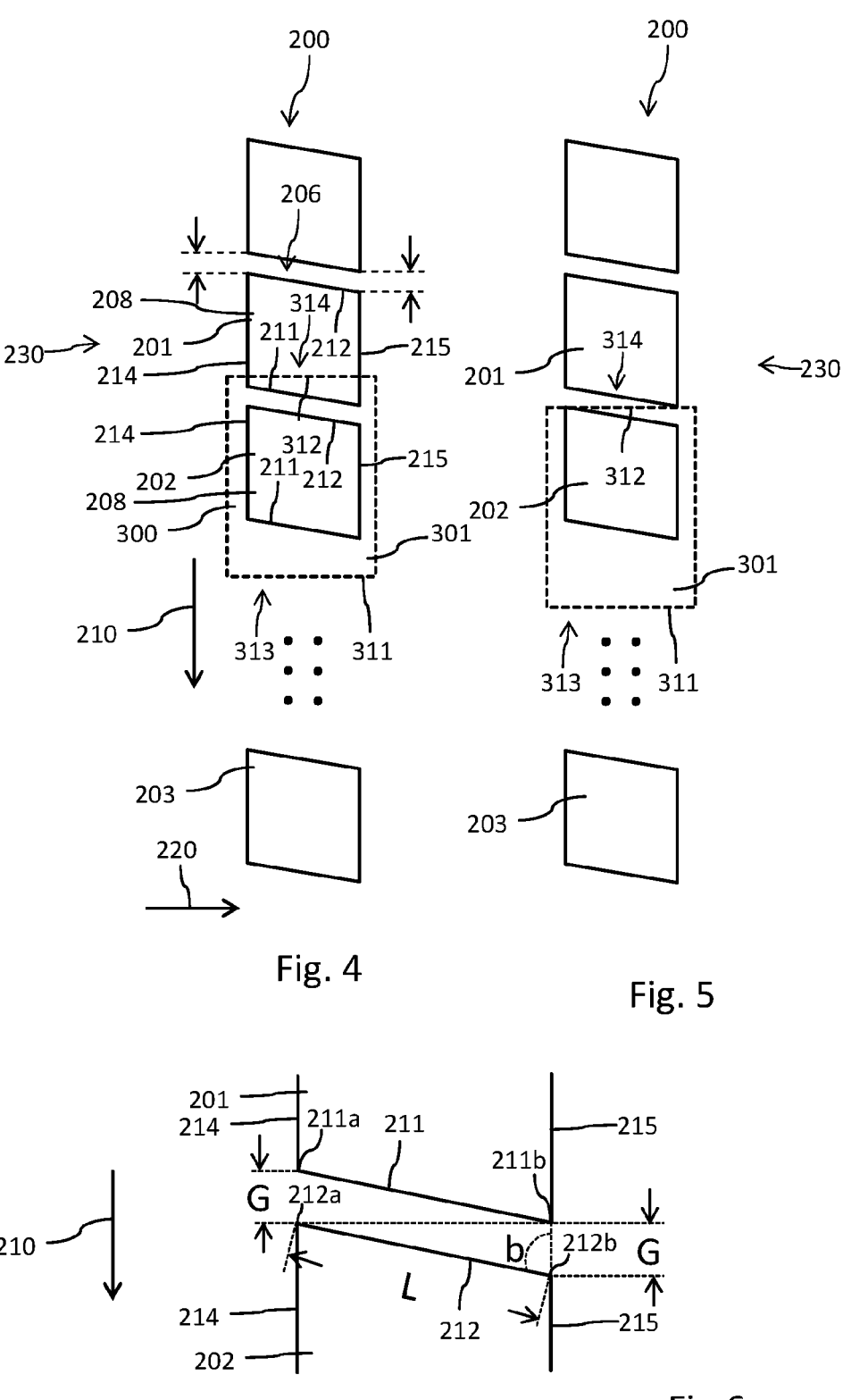
FIG. 4 shows in detail the configuration and design of the detector arrangement, FIG. 5 as a further illustration of the detector arrangement with the object moved further along the first direction compared to the configuration of FIG. 4.
FIG. 6 is an enlarged and detailed view of the gap between a first and a second detector.

The position or the shadow of the stopper 109 is illustrated as an object 300 with a dashed line in FIGS. 4 and 5. The object 300, typically in form of the tubular shaped stopper 109 includes a front face 313 and an oppositely located rear face 314. In the illustration of FIGS. 4 and 5, which is a side view on the object 300 as it moves in the first direction 200 and relative to the detector arrangement 200, only a rear edge 312 and a front edge 311 that coincide with the respective rear and front faces 314, 313 are illustrated.

Moreover, in FIGS. 4 and 5 only a front edge 311 of a body 301 of the object 300 is illustrated. The object 300 is representative of a shadow of the stopper 109 relative to the detector row 230 of the detector arrangement 200. Alternatively and when operated in a reflection mode, the object 300 is representative of a spatial pattern of electromagnetic radiation reflected from the stopper 109.

As indicated in FIGS. 4 and 5 at least one of the first detection front edge 211 and the first detection rear edge 212 extends non-parallel to at least one of the front edge 311 and the rear edge 312 of the object 300. The first detection front edge 211 and/or the first detection rear edge 212 extend at a non-zero angle with regard to the elongation of one of the front edge 311 and the rear edge 312 of the object 300.

At least one or both of the front edge 311 and the rear edge 312 extend substantially perpendicular to the first direction 210 which represents a direction of movement of the stopper 109 relative to the barrel 107 of the cartridge 106. In this way and due to the non-parallel arrangement or orientation of the first detection front edge and/or the first detection rear edge a rather smooth and continues modification of an electric signal generated by the detector 201 can be achieved as the front edge 311 or rear edge 312 passes or traverses one of the first detection front edge 211 and the first detection rear edge 212 during a movement of the object 300 relative to the detector arrangement 200.

In a configuration as illustrated in FIG. 4 and wherein the rear edge 312 of the object 300 is close to the first longitudinal end 211a of the first detection front edge 211 a further movement of the object 300 in the first direction 210 leads to a configuration in which the object 300 no longer overlaps with that part or section of the detection area 208 that is in close vicinity to the crossing point of the first side edge 214 at the first detection front edge 211. Here and due to the tilted or non-parallel alignment of the first detection front edge 211 at least a portion of the front edge 211 close to the second side edge 215 will still be covered by the object 300.

Consequently and as the object 300 is subject to a further constant movement in the first direction 210 relative to the detector arrangement 200 the smooth crossing of at least one of the front edge 311 and the rear edge 312 across at least one of the tilted first detection front edge 211 and the first detection rear edge 212 can be precisely detected on the basis of a signal amplitude the first detector.

Figure 8:
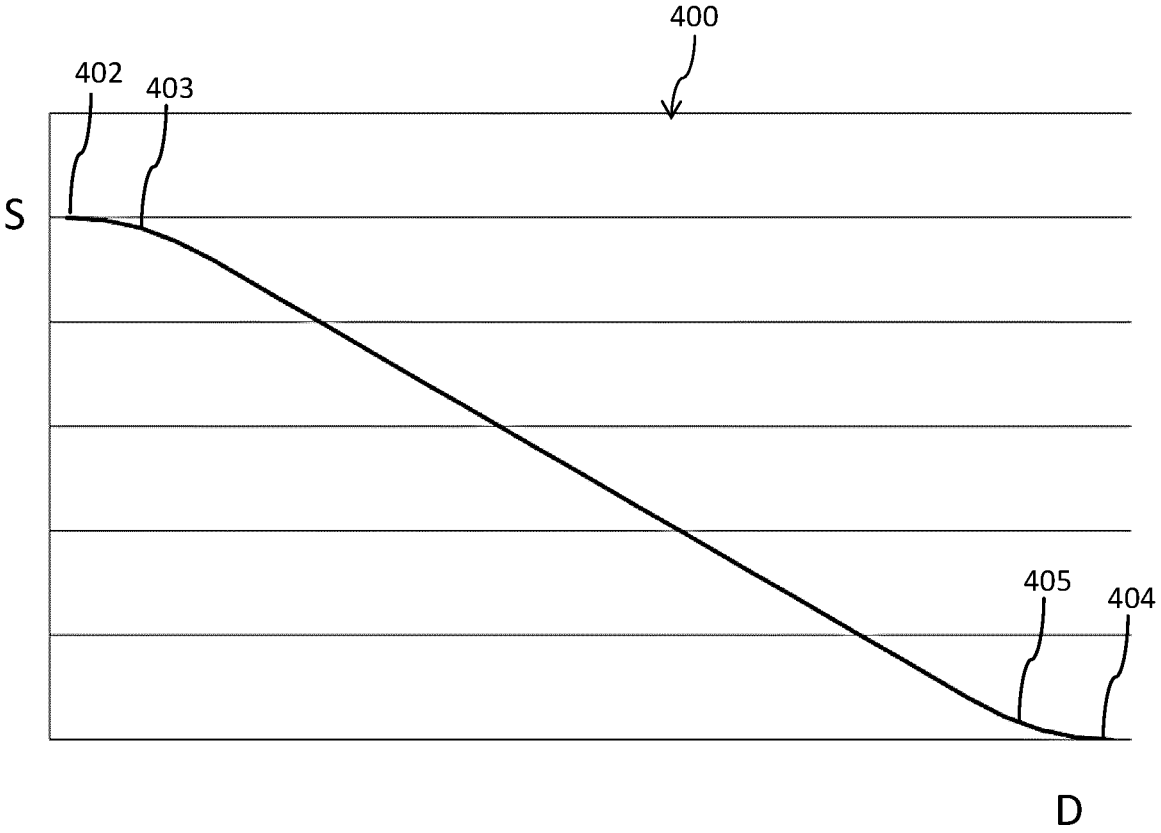
FIG. 8 shows a diagram illustrating the signal output of a detector versus displacement of the object.

In FIG. 8, one example of a constant decrease of a signal amplitude of the first detector 201 is illustrated as the object 300 is moved in the first direction 201 relative to the detector arrangement. The graph 400 illustrates a normalized signal strength S over the moving distance D of the object 300 relative to the detector arrangement 200.

At a position 402 the object 300 completely overlaps with the detection area 208 of the first detector 200. At the position 404 there is no mutual overlap of the object 300 and the first detection area 208. Between the position 402 and 403 there is a slight decrease of overlap, namely as the rear edge 312 crosses the third detector rear edge in the first direction 210. As it is apparent in the region between the positions 402 and 403 the rate of decrease of the signal strength S over the moving distance D is quite small and constantly increases. At the position 403 the rear edge 312 of the object 300 has passed the first detection rear edge 212. Between the positions 403 and 405 there is a constant degree of the signal strength over the moving distance.

At the position 405 the rear edge 312 of the object starts to traverse the first detection front edge 211 of the first detector 201. This traversing is completed and there is no mutual overlap any longer when arriving in position 404. Between the position 405 and the position 404 there is a constant decrease of the rate of the modification of the signal strength over the moving distance D.

The detector arrangement 200 includes a second detector 202 arranged in line to the first detector 201 along and with regards to the first direction 210. The second detector 202 is of equal shape compared to the first detector 201. All detectors 201, 202, 203 of the detector arrangement 200 can be arranged in line and hence flush in the first direction 210. They form an elongated straight shaped detector row 230. The second detector 202 is arranged at a predefined gap size G in the first direction 210 with regard to the first detector 201. Hence, the second detector 202 is arranged at a predefined, e.g. constant distance from the first detector 201. In this way, a gap 206 of predefined size is formed between consecutively and adjacently arranged detectors 201, 202, 203 and so on. The numerous detectors 201, 202, 203 are arranged equidistantly in the first direction 210.

The second detector also includes a second detection area 208 confined in the first direction 210 by a second detection front edge 211 and by a second detection rear edge 212. The second detection rear edge 212 faces towards the first detection front edge 211 of the first detector 201. The second detector front edge 211 faces towards a third detection rear edge of a third detector 203 and so on.

The first side edge 214 of the second detection area 208 is flush and aligns with the first side edge 214 of the first detection area 208. The same is valid for the second side edges 215 of the detection areas 208 of the first and the second detectors 201, 202. The first detection front edge 211 and the first detection rear edge 212 extend parallel to each other. The same is valid for the second detection front edge 211 and the second detection rear edge 212.

As indicated in more detail in FIG. 6, the position of the first end 211a of the first detection front edge 211 of the first detector 201 is shifted and is offset in the first direction 210 from a second end 211b of the first detection front edge 211. As illustrated in FIG. 6 the second end 211b of the first detection front edge 211 of the first detector 201 coincides or adjoins in the first direction 210 with the first end 212a of the second detection rear edge 212 of the second detector 202. In this way and as the object 300 is constantly moved in the first direction 201 there will be no configuration, in which the entirety of a front edge 311 and a rear edge 312 would disappear in a gap 206 between consecutively arranged detectors 201, 202, 203.

For instance when a rear edge 312 of the object arrived at a corner section of the second side edge 215 and the first detection front edge 211 of the first detector 201 it will be simultaneously in an overlapping configuration with a corner of a first side edge 214 and the second detection rear edge 212 of the second detector 202. In terms of the diagram 400 as illustrated in FIG. 8, the position 404 of the first detector 201 overlaps with the position 402 of a second detector 202. In this way and for each available position of the object with regard to the first direction 210 there will be an unequivocal combination of signals from the numerous detectors 201, 202, 203 of the detector arrangement 200.

This configuration is reflected in FIG. 5. With regards to the first detector 201 a configuration as described with regard to position 404 has been reached for the first detector 201. This configuration overlaps and coincides with position 402 with regards to the second detector 202.

FIG. 6 the mutual relationship between the gap size G the length L of the first detection front edge 211 and/or the second detection rear edge 212 as well as the angle b between the first direction 210 and the direction of the first detection front edge 211 and/or the first detection rear edge 212 is illustrated. A size G of the gap substantially equals $G = L \sin(90° - b)$.

LIST OF REFERENCE NUMBERS 2 distal direction
3 proximal direction
100 drug delivery device
101 drive mechanism
102 injection device
104 position detector
105 flexible substrate
106 cartridge
106*a* outlet
107 barrel
108 piston rod
108*a* plunger head
109 stopper
110 housing
111 injection button
112 dosage knob
113 needle
114 window
115 needle assembly
116 needle cap
117 outer needle cap
118 cap
124 light source
124*a* light-emitting element
124*b* light-emitting element
125 light guiding structure
126*a* photodiode
126*b* photodiode
128 processor
130 antenna
132 temperature sensor
133 code generator circuit
134 power management unit
135 memory 137 communication front end
138 data transfer module
140 functional electronic module
141 central processing unit
142 analog-digital converter
162 interrogator
164 RF module
166 transmitter
168 receiver
170 processor
172 external device
200 detector arrangement
201 detector
202 detector
203 detector
206 gap
208 detection area
210 first direction
211 front edge
211*a* first end
212*b* second end
212 rear edge
212*a* first end
212*b* second end
214 side edge
215 side edge
220 second direction
230 detector row
300 object
301 body
311 front edge
312 rear edge
313 front face
314 rear face

The invention claimed is:

1. A detector arrangement for detecting a position of an object with regard to a first direction of movement, the detector arrangement comprising:

a first detector configured to detect electromagnetic radiation, the first detector comprising a first detection area sensitive to the electromagnetic radiation, wherein the detection area is confined by a first detection front edge and by a first detection rear edge, wherein the first detection front edge is separated from the first detection rear edge in the first direction, wherein the object comprises a front edge and a rear edge separated from each other in the first direction and wherein the object is movable relative to the detector arrangement with regard to the first direction, and wherein at least one of the first detection front edge and the first detection rear edge extends non-parallel to at least one of the front edge and the rear edge of the object.

2. The detector arrangement of claim 1, further comprising a second detector configured to detect the electromagnetic radiation, wherein the second detector is separated from the first detector in the first direction and wherein a gap is formed between the first detector and the second detector.

3. The detector arrangement of claim 2, wherein the second detector is arranged in line to the first detector with regard to the first direction.

4. The detector arrangement of claim 2, wherein the second detector comprises a second detection area sensitive to the electromagnetic radiation, wherein the second detection area is confined by a second detection front edge and by a second detection rear edge, wherein the second detection front edge is separated from the second detection rear edge in the first direction and wherein at least one of the second detection front edge and the second detection rear edge extends non-parallel to at least one of the front edge and the rear edge of the object.

5. The detector arrangement of claim 1, wherein the first detection front edge at least in sections extends parallel to the first detection rear edge.

6. The detector arrangement of claim 1, wherein the first detection front edge comprises a first end adjoining a first lateral side edge of the first detection area and wherein the first detection front edge comprises a second end adjoining a second lateral side edge of the first detection area.

7. The detector arrangement of claim 4, wherein the second detection rear edge comprises a first end adjoining a first lateral side edge of the second detection area and wherein the second detection rear edge comprises a second end adjoining a second lateral side edge of the second detection area and:
   wherein a position of a first end of the first detection front edge with regard to the first direction overlaps or adjoins with a position of the second end of the second detection rear edge with regard to the first direction, wherein the first end of the first detection front edge adjoins a first lateral side edge of the first detection area, or
   wherein a position of a second end of the first detection front edge with regard to the first direction overlaps or adjoins with a position of the first end of the second detection rear edge with regard to the first direction, wherein the second end of the first detection front edge adjoins a second lateral side edge of the first detection area.

8. The detector arrangement of claim 2, wherein at least one of the first detection front edge and the first detection rear edge extends at an angle b with regard to the first direction and wherein a size G of the gap substantially equals G=L sin(90°−b), with L being a length of one of the first detection front edge and the first detection rear edge.

9. The detector arrangement of claim 2, comprising a plurality of first detectors forming a longitudinal detector row extending along the first direction.

10. A position detector for determining a position of a stopper in a cartridge with regard to a first direction, the position detector comprises:
   a flexible substrate configured to be wrapped around a barrel of the cartridge;
   a detector arrangement arranged on the flexible substrate, the detector arrangement comprising a first detector configured to detect electromagnetic radiation, the first detector comprising a first detection area sensitive to the electromagnetic radiation, wherein the detection area is confined by a first detection front edge and by a first detection rear edge, wherein the first detection front edge is separated from the first detection rear edge in the first direction, wherein an object comprises a front edge and a rear edge separated from each other in the first direction and wherein the object is movable relative to the detector arrangement with regard to the first direction, and wherein at least one of the first detection front edge and the first detection rear edge extends non-parallel to at least one of the front edge and the rear edge of the object, wherein the position of the object is the position of the stopper, and wherein the stopper is slidably arranged inside the cartridge with regard to the first direction and wherein the cartridge is configured to accommodate a liquid medicament;
   at least one light source configured to emit electromagnetic radiation onto or through the barrel; and a microprocessor arranged on the flexible substrate, connected to the detector arrangement and operable to determine a position of the stopper with regard to the first direction on the basis of an electric signal received from the detector arrangement when exposed to the electromagnetic radiation.

11. The position detector of claim 10, wherein the at least one light source is arranged on the flexible substrate and wherein the at least one light source comprises a plurality of light-emitting elements separated from each other in the first direction.

12. The position detector of claim 10, wherein the at least one light source comprises at least one light-emitting element and a longitudinally extending light guiding structure optically coupled with the at least one light-emitting element, wherein the longitudinally extending light guiding structure extends substantially parallel to the first direction.

13. The position detector of claim 10, further comprising a second detector configured to detect the electromagnetic radiation, wherein the second detector is separated from the first detector in the first direction and wherein a gap is formed between the first detector and the second detector.

14. The position detector of claim 13, wherein the second detector is arranged in line to the first detector with regard to the first direction.

15. The position detector of claim 13, wherein the second detector comprises a second detection area sensitive to the electromagnetic radiation, wherein the second detection area is confined by a second detection front edge and by a second detection rear edge, wherein the second detection front edge is separated from the second detection rear edge in the first direction and wherein at least one of the second detection front edge and the second detection rear edge extends non-parallel to at least one of the front edge and the rear edge of the object.

16. The position detector of claim 12, wherein the first detection front edge at least in sections extends parallel to the first detection rear edge.

17. A cartridge for a liquid medicament, the cartridge comprising:
   an elongated barrel extending along a first direction;
   a stopper arranged inside the barrel and being displaceable relative to the barrel along the first direction for expelling the liquid medicament; and
   a position detector wrappable around the barrel, wherein the position detector comprises:
   a flexible substrate configured to be wrapped around a barrel of the cartridge,
   a detector arrangement arranged on the flexible substrate, the detector arrangement comprising a first detector configured to detect electromagnetic radiation, the first detector comprising a first detection area sensitive to the electromagnetic radiation, wherein the first detection area is confined by a first detection front edge and by a first detection rear edge, wherein the first detection front edge is separated from the first detection rear edge in the first direction, wherein the stopper is slidably arranged inside the cartridge and movable relative to the detector arrangement with regard to the first direction, wherein the stopper comprises a front edge and a rear edge separated from each other in the first direction, and wherein at least one of the first detection front edge and the first detection rear edge extends non-parallel to at least one of the front edge and the rear edge of the stopper, at least one light source configured to emit electromagnetic radiation onto or through the barrel; and a microprocessor arranged on the flexible substrate, connected to the detector arrangement and operable to determine a position of the stopper with regard to the first direction on the basis of an electric signal received from the detector arrangement when exposed to the electromagnetic radiation.

18. The cartridge of claim 17, wherein the at least one light source is located diametrically opposite to the detector arrangement when the position detector is wrapped around the barrel and wherein the stopper is located between the at least one light source and the detector arrangement of the position detector.

19. The cartridge of claim 17, wherein the at least one light source is arranged on the flexible substrate and wherein the at least one light source comprises a plurality of light-emitting elements separated from each other in the first direction and a longitudinally extending light guiding structure optically coupled with the plurality of light-emitting elements, wherein the longitudinally extending light guiding structure extends substantially parallel to the first direction.

20. A drug delivery device comprising:

a drive mechanism comprising a piston rod configured to expel a liquid medicament from a cartridge, wherein the cartridge comprises a barrel and a stopper, wherein the stopper is arranged inside the barrel and wherein the stopper is displaceable relative to the barrel along a first direction for expelling the liquid medicament;

a housing configured to accommodate the cartridge; and a position detector according to claim 10.

* * * * *